United States Patent
Smith et al.

(10) Patent No.: US 9,694,122 B2
(45) Date of Patent: *Jul. 4, 2017

(54) RIGID BODY AORTIC BLOOD PUMP IMPLANT

(71) Applicant: L-VAD Technology, Inc., Detroit, MI (US)

(72) Inventors: Robert M Smith, Detroit, MI (US); Adrian Kantrowitz, Detroit, MI (US); Valluvan Jeevanandam, Detroit, MI (US); Allen B. Kantrowitz, Detroit, MI (US); Paul S. Freed, Detroit, MI (US)

(73) Assignee: L-VAD Technology, Inc., Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/277,031

(22) Filed: May 13, 2014

(65) Prior Publication Data

US 2014/0364680 A1 Dec. 11, 2014

Related U.S. Application Data

(63) Continuation of application No. 12/120,457, filed on May 14, 2008, now Pat. No. 8,721,515, and a continuation-in-part of application No. 10/770,269, filed on Feb. 2, 2004, now Pat. No. 8,540,618.

(60) Provisional application No. 60/944,292, filed on Jun. 15, 2007, provisional application No. 60/444,077, filed on Jan. 31, 2003, provisional application No. 60/477,740, filed on Jun. 12, 2003.

(51) Int. Cl.
*A61M 1/12* (2006.01)
*A61M 1/10* (2006.01)

(52) U.S. Cl.
CPC .......... *A61M 1/107* (2013.01); *A61M 1/1072* (2013.01); *A61M 1/122* (2014.02)

(58) Field of Classification Search
None
See application file for complete search history.

(56) References Cited

U.S. PATENT DOCUMENTS 3,585,983 A * 6/1971 Kantrowitz et al. ............ 600/18
3,698,381 A * 10/1972 Federico et al. ................ 600/17
3,720,199 A * 3/1973 Rishton et al. ................. 600/18
3,720,200 A * 3/1973 Laird .............................. 600/18

(Continued)

FOREIGN PATENT DOCUMENTS

EP 234046 A1 * 9/1987
EP 363203 A2 * 4/1990
EP 449786 A1 * 10/1991

*Primary Examiner* — Erica Lee
(74) *Attorney, Agent, or Firm* — Avery N. Goldstein; Blue Filament Law PLLC

(57) ABSTRACT

An implantable aortic blood pump includes a rigid body having wall extending along a long axis and defining an inflation port portion with an inflation aperture therethrough. The aperture is fluid communication with an inner surface of the body and on a fluid supply, the body is preferably independent of an external brace or an external stiffener, yet still has a cantilevered deformation of less than 8 millimeters in response to a 200 gram weight suspended from a front body edge. A deflecting structure of a membrane deflects in response to fluid pressure so as to pump blood when the pump is secured to a subject aorta.

7 Claims, 3 Drawing Sheets

(56) References Cited

U.S. PATENT DOCUMENTS

| | | | | |
|---|---|---|---|---|
| 3,769,960 A * | 11/1973 | Robinson | | 600/18 |
| 3,939,820 A * | 2/1976 | Grayzel | | 600/18 |
| 3,985,123 A * | 10/1976 | Herzlinger et al. | | 600/526 |
| 4,014,317 A * | 3/1977 | Bruno | | 600/18 |
| 4,016,871 A * | 4/1977 | Schiff | | 600/510 |
| 4,058,855 A * | 11/1977 | Runge | | 623/3.18 |
| 4,080,958 A * | 3/1978 | Bregman et al. | | 600/16 |
| 4,116,589 A * | 9/1978 | Rishton | | 417/384 |
| 4,195,623 A * | 4/1980 | Zeff et al. | | 600/18 |
| 4,204,524 A * | 5/1980 | Martin et al. | | 600/17 |
| 4,222,127 A * | 9/1980 | Donachy et al. | | 623/3.21 |
| 4,261,339 A * | 4/1981 | Hanson et al. | | 600/18 |
| 4,276,874 A * | 7/1981 | Wolvek et al. | | 600/18 |
| 4,311,133 A * | 1/1982 | Robinson | | 600/18 |
| 4,314,550 A * | 2/1982 | Apstein | | 600/16 |
| 4,327,709 A * | 5/1982 | Hanson et al. | | 600/18 |
| 4,346,698 A * | 8/1982 | Hanson et al. | | 600/18 |
| 4,362,150 A * | 12/1982 | Lombardi, Jr. et al. | | 600/18 |
| 4,376,312 A * | 3/1983 | Robinson et al. | | |
| 4,402,307 A * | 9/1983 | Hanson et al. | | 600/18 |
| 4,407,271 A * | 10/1983 | Schiff | | 600/17 |
| 4,422,447 A * | 12/1983 | Schiff | | 600/18 |
| 4,444,186 A * | 4/1984 | Wolvek et al. | | 606/194 |
| 4,467,790 A * | 8/1984 | Schiff | | 600/18 |
| 4,473,067 A * | 9/1984 | Schiff | | 600/18 |
| 4,515,587 A * | 5/1985 | Schiff | | 600/18 |
| 4,522,194 A * | 6/1985 | Normann | | 600/18 |
| 4,522,195 A * | 6/1985 | Schiff | | 600/18 |
| 4,527,549 A * | 7/1985 | Gabbay | | 600/18 |
| 4,531,512 A * | 7/1985 | Wolvek et al. | | 600/18 |
| 4,531,936 A * | 7/1985 | Gordon | | 604/500 |
| 4,540,404 A * | 9/1985 | Wolvek | | 604/103.05 |
| 4,541,417 A * | 9/1985 | Krikorian | | 600/17 |
| 4,546,759 A * | 10/1985 | Solar | | 600/18 |
| 4,552,127 A * | 11/1985 | Schiff | | 600/18 |
| 4,569,332 A * | 2/1986 | Schiff et al. | | 600/18 |
| 4,576,142 A * | 3/1986 | Schiff | | 600/18 |
| 4,583,523 A * | 4/1986 | Kleinke et al. | | 600/16 |
| 4,584,989 A * | 4/1986 | Stith | | 600/18 |
| 4,592,340 A * | 6/1986 | Boyles | | 600/18 |
| 4,630,597 A * | 12/1986 | Kantrowitz et al. | | 600/18 |
| 4,644,936 A * | 2/1987 | Schiff | | 600/18 |
| 4,646,719 A * | 3/1987 | Neuman et al. | | 600/18 |
| 4,681,092 A * | 7/1987 | Cho et al. | | 600/18 |
| 4,685,446 A * | 8/1987 | Choy | | 600/18 |
| 4,697,573 A * | 10/1987 | Schiff | | 600/18 |
| 4,697,574 A * | 10/1987 | Karcher et al. | | 600/17 |
| 4,733,652 A * | 3/1988 | Kantrowitz et al. | | 600/18 |
| 4,741,328 A * | 5/1988 | Gabbay | | 600/18 |
| 4,753,221 A * | 6/1988 | Kensey et al. | | 600/16 |
| 4,771,765 A * | 9/1988 | Choy et al. | | 600/18 |
| 4,785,795 A * | 11/1988 | Singh | | 600/18 |
| 4,787,368 A * | 11/1988 | Kageyama | | 600/18 |
| 4,794,910 A * | 1/1989 | Mushika | | 600/18 |
| 4,804,358 A * | 2/1989 | Karcher et al. | | 600/17 |
| 4,809,676 A * | 3/1989 | Freeman | | 600/16 |
| 4,809,681 A * | 3/1989 | Kantrowitz et al. | | 600/17 |
| 4,813,952 A * | 3/1989 | Khalafalla | | 623/3.12 |
| 4,827,906 A * | 5/1989 | Robicsek et al. | | 600/17 |
| 4,846,831 A * | 7/1989 | Skillin | | 623/3.1 |
| 4,861,330 A * | 8/1989 | Voss | | 600/18 |
| 4,863,461 A * | 9/1989 | Jarvik | | |
| 4,897,077 A * | 1/1990 | Cicciu et al. | | 600/18 |
| 4,902,272 A * | 2/1990 | Milder et al. | | 600/18 |
| 4,902,273 A * | 2/1990 | Choy et al. | | 600/18 |
| 4,906,229 A * | 3/1990 | Wampler | | 600/16 |
| 4,925,443 A * | 5/1990 | Heilman et al. | | 600/16 |
| 4,931,036 A * | 6/1990 | Kanai et al. | | 600/18 |
| 4,943,275 A * | 7/1990 | Stricker | | 600/18 |
| 4,979,936 A * | 12/1990 | Stephenson et al. | | 600/16 |
| 4,985,014 A * | 1/1991 | Orejola | | 600/16 |
| 4,994,018 A * | 2/1991 | Saper | | 600/18 |
| 4,994,078 A * | 2/1991 | Jarvik | | 623/3.14 |
| 5,004,472 A * | 4/1991 | Wallace | | 606/194 |
| 5,006,104 A * | 4/1991 | Smith et al. | | 600/16 |
| 5,011,468 A * | 4/1991 | Lundquist et al. | | |
| 5,024,668 A * | 6/1991 | Peters et al. | | 606/194 |
| 5,045,051 A * | 9/1991 | Milder et al. | | 600/16 |
| 5,090,957 A * | 2/1992 | Moutafis et al. | | 600/18 |
| 5,092,879 A * | 3/1992 | Jarvik | | 623/3.3 |
| 5,116,305 A * | 5/1992 | Milder et al. | | 600/18 |
| 5,120,299 A * | 6/1992 | Lombardi | | 600/18 |
| 5,129,878 A * | 7/1992 | Takano et al. | | 600/18 |
| 5,135,467 A * | 8/1992 | Citron | | 600/16 |
| 5,158,529 A * | 10/1992 | Kanai | | 600/18 |
| 5,167,628 A * | 12/1992 | Boyles | | 604/103.07 |
| 5,169,378 A * | 12/1992 | Figuera | | 600/16 |
| 5,169,379 A * | 12/1992 | Freed et al. | | 600/18 |
| 5,171,207 A * | 12/1992 | Whalen | | 600/16 |
| 5,176,619 A * | 1/1993 | Segalowitz | | 600/18 |
| 5,195,942 A * | 3/1993 | Weil et al. | | 600/18 |
| 5,222,980 A * | 6/1993 | Gealow | | 623/3.12 |
| 5,230,692 A * | 7/1993 | Kanai | | 600/18 |
| 5,242,374 A * | 9/1993 | Isoyama et al. | | 600/18 |
| 5,254,090 A * | 10/1993 | Lombardi et al. | | 604/96.01 |
| 5,267,940 A * | 12/1993 | Moulder | | 600/16 |
| 5,273,518 A * | 12/1993 | Lee et al. | | 600/18 |
| 5,290,227 A * | 3/1994 | Pasque | | 600/16 |
| 5,300,017 A * | 4/1994 | Isoyama et al. | | 600/18 |
| 5,300,113 A * | 4/1994 | Arpesella et al. | | 623/3.21 |
| 5,308,319 A * | 5/1994 | Ide et al. | | 600/18 |
| 5,318,501 A * | 6/1994 | Lee et al. | | 600/16 |
| 5,330,451 A * | 7/1994 | Gabbay | | 604/284 |
| 5,330,524 A * | 7/1994 | Mar | | 607/129 |
| 5,334,142 A * | 8/1994 | Paradis | | 604/509 |
| 5,344,385 A * | 9/1994 | Buck et al. | | 600/16 |
| 5,365,933 A * | 11/1994 | Elghazzawi | | 600/510 |
| 5,380,267 A * | 1/1995 | Boutelle et al. | | 600/18 |
| 5,409,444 A * | 4/1995 | Kensey et al. | | 600/18 |
| 5,411,027 A * | 5/1995 | Wiklund et al. | | 600/439 |
| 5,413,549 A * | 5/1995 | Leschinsky | | 600/18 |
| 5,413,558 A * | 5/1995 | Paradis | | 604/101.05 |
| 5,421,807 A * | 6/1995 | Atsumi | | 600/16 |
| RE34,993 E * | 7/1995 | Cicciu et al. | | 600/18 |
| 5,429,584 A * | 7/1995 | Chiu | | 600/18 |
| 5,443,504 A * | 8/1995 | Hill | | 623/3.12 |
| 5,453,076 A * | 9/1995 | Kiyota et al. | | 600/18 |
| 5,479,946 A * | 1/1996 | Trumble | | 128/899 |
| 5,484,385 A * | 1/1996 | Rishton | | 600/16 |
| 5,498,228 A * | 3/1996 | Royalty et al. | | 600/16 |
| 5,514,073 A * | 5/1996 | Miyata et al. | | 600/18 |
| 5,531,776 A * | 7/1996 | Ward et al. | | 607/105 |
| 5,647,380 A * | 7/1997 | Campbell et al. | | 128/898 |
| 5,653,676 A * | 8/1997 | Buck et al. | | 600/16 |
| 5,678,570 A * | 10/1997 | Manning | | 128/897 |
| 5,683,347 A * | 11/1997 | Miyata et al. | | 600/18 |
| 5,688,245 A * | 11/1997 | Runge | | 604/151 |
| 5,701,919 A * | 12/1997 | Buck et al. | | 128/898 |
| 5,704,891 A * | 1/1998 | Mussivand | | 600/16 |
| 5,711,754 A * | 1/1998 | Miyata et al. | | 600/18 |
| 5,716,318 A * | 2/1998 | Manning | | 600/16 |
| 5,718,248 A * | 2/1998 | Trumble et al. | | 128/899 |
| 5,722,930 A * | 3/1998 | Larson, Jr. et al. | | 600/16 |
| 5,755,687 A * | 5/1998 | Donlon | | 604/508 |
| 5,758,664 A * | 6/1998 | Campbell et al. | | 128/898 |
| 5,759,148 A * | 6/1998 | Sipin | | 600/18 |
| 5,772,631 A * | 6/1998 | Lepor | | 604/96.01 |
| 5,817,001 A * | 10/1998 | Leschinsky et al. | | 600/18 |
| 5,820,542 A * | 10/1998 | Dobak et al. | | 600/16 |
| 5,827,171 A * | 10/1998 | Dobak, III et al. | | 600/16 |
| 5,848,962 A * | 12/1998 | Feindt et al. | | 600/16 |
| 5,865,721 A * | 2/1999 | Andrews et al. | | 600/18 |
| 5,888,186 A * | 3/1999 | Trumble et al. | | 600/18 |
| 5,910,103 A * | 6/1999 | Saper et al. | | 600/18 |
| 5,913,814 A * | 6/1999 | Zantos | | 600/18 |
| 5,928,132 A * | 7/1999 | Leschinsky | | 600/16 |
| 5,980,448 A * | 11/1999 | Heilman et al. | | 600/16 |
| 5,984,857 A * | 11/1999 | Buck et al. | | 600/18 |
| 6,004,258 A * | 12/1999 | Watari et al. | | 600/18 |
| 6,007,479 A * | 12/1999 | Rottenberg et al. | | 600/16 |
| 6,024,693 A * | 2/2000 | Schock et al. | | 600/18 |
| 6,030,335 A * | 2/2000 | Franchi | | 600/16 |
| 6,030,336 A * | 2/2000 | Franchi | | 600/18 |
| 6,042,532 A * | 3/2000 | Freed et al. | | 600/18 |

(56) References Cited

U.S. PATENT DOCUMENTS

| | | | |
|---|---|---|---|
| 6,045,496 A * | 4/2000 | Pacella et al. | 600/16 |
| 6,050,932 A * | 4/2000 | Franchi | 600/16 |
| 6,056,723 A * | 5/2000 | Donlon | 604/102.01 |
| 6,060,454 A * | 5/2000 | Duhaylongsod | 514/26 |
| 6,066,085 A * | 5/2000 | Heilman et al. | 600/16 |
| 6,083,260 A * | 7/2000 | Aboul-Hosn | 623/3.14 |
| 6,087,394 A * | 7/2000 | Duhaylongsod | 514/478 |
| 6,090,096 A * | 7/2000 | St. Goar et al. | 604/509 |
| 6,120,431 A * | 9/2000 | Magovern et al. | 600/17 |
| 6,127,410 A * | 10/2000 | Duhaylongsod | 514/478 |
| 6,132,363 A * | 10/2000 | Freed et al. | 600/16 |
| 6,132,364 A * | 10/2000 | Rottenberg et al. | 600/16 |
| 6,136,025 A * | 10/2000 | Barbut et al. | 623/3.1 |
| 6,149,578 A * | 11/2000 | Downey et al. | 600/18 |
| 6,179,793 B1 * | 1/2001 | Rothman et al. | 601/44 |
| 6,186,149 B1 * | 2/2001 | Pacella et al. | 128/898 |
| 6,190,304 B1 * | 2/2001 | Downey et al. | 600/16 |
| 6,191,111 B1 * | 2/2001 | Leschinsky | 514/12 |
| 6,200,260 B1 * | 3/2001 | Bolling | 600/16 |
| 6,210,318 B1 * | 4/2001 | Lederman | 600/18 |
| 6,210,319 B1 * | 4/2001 | Williams et al. | 600/18 |
| 6,228,018 B1 * | 5/2001 | Downey et al. | 600/16 |
| 6,231,498 B1 * | 5/2001 | Pfeiffer et al. | 600/18 |
| 6,241,706 B1 * | 6/2001 | Leschinsky et al. | 604/99.01 |
| 6,245,008 B1 * | 6/2001 | Leschinsky et al. | 600/18 |
| 6,290,641 B1 * | 9/2001 | Nigroni et al. | 600/18 |
| 6,296,605 B1 * | 10/2001 | Michelman et al. | 600/16 |
| 6,299,575 B1 * | 10/2001 | Bolling | 600/16 |
| 6,387,037 B1 * | 5/2002 | Bolling et al. | 600/16 |
| 6,390,969 B1 * | 5/2002 | Bolling et al. | 600/16 |
| 6,398,715 B1 * | 6/2002 | Magovern et al. | 600/16 |
| 6,406,422 B1 * | 6/2002 | Landesberg | 600/17 |
| 6,414,018 B1 * | 7/2002 | Duhaylongsod | 514/478 |
| 6,423,031 B1 * | 7/2002 | Donlon | 604/102.01 |
| 6,428,464 B1 * | 8/2002 | Bolling | 600/16 |
| 6,440,059 B1 * | 8/2002 | Haas et al. | 600/18 |
| 6,468,200 B1 * | 10/2002 | Fischi | 600/16 |
| 6,471,633 B1 * | 10/2002 | Freed | 600/16 |
| 6,511,412 B1 * | 1/2003 | Freed et al. | 600/17 |
| 6,511,413 B2 * | 1/2003 | Landesberg | 600/17 |
| 6,514,226 B1 * | 2/2003 | Levin et al. | 604/9 |
| 6,532,964 B2 * | 3/2003 | Aboul-Hosn et al. | 128/898 |
| 6,536,260 B2 * | 3/2003 | Williams | 73/40 |
| 6,547,821 B1 * | 4/2003 | Taylor et al. | 623/3.1 |
| 6,579,223 B2 * | 6/2003 | Palmer | 600/16 |
| 6,585,635 B1 * | 7/2003 | Aldrich | 600/16 |
| 6,610,004 B2 * | 8/2003 | Viole et al. | 600/16 |
| 6,616,597 B2 * | 9/2003 | Schock et al. | 600/18 |
| 6,616,598 B2 * | 9/2003 | Kaushansky et al. | 600/18 |
| 6,632,169 B2 * | 10/2003 | Korakianitis et al. | 600/18 |
| 6,666,814 B2 * | 12/2003 | Downey et al. | 600/18 |
| 6,669,624 B2 * | 12/2003 | Frazier | 600/18 |
| 6,679,829 B2 * | 1/2004 | Nigroni et al. | 600/18 |
| 6,685,621 B2 * | 2/2004 | Bolling et al. | 600/16 |
| 6,709,383 B2 * | 3/2004 | Tsukahara et al. | 600/16 |
| 6,711,436 B1 * | 3/2004 | Duhaylongsod | 607/9 |
| 6,735,532 B2 * | 5/2004 | Freed et al. | 702/50 |
| 6,800,068 B1 * | 10/2004 | Dae et al. | 604/113 |
| 6,808,484 B1 * | 10/2004 | Peters et al. | 600/18 |
| 6,827,682 B2 * | 12/2004 | Bugge et al. | 600/16 |
| 6,863,648 B2 * | 3/2005 | Williams et al. | 600/18 |
| 6,974,409 B2 * | 12/2005 | Verkerke et al. | |
| 7,229,402 B2 * | 6/2007 | Diaz et al. | |
| 2001/0016676 A1 * | 8/2001 | Williams et al. | 600/18 |
| 2001/0031907 A1 * | 10/2001 | Downey et al. | 600/18 |
| 2001/0034469 A1 * | 10/2001 | Nigroni et al. | 600/18 |
| 2001/0037048 A1 * | 11/2001 | Pfeiffer et al. | 600/18 |
| 2002/0002321 A1 * | 1/2002 | Tsukahara et al. | 600/16 |
| 2002/0045795 A1 * | 4/2002 | Aboul-Hosn et al. | 600/16 |
| 2002/0072647 A1 * | 6/2002 | Schock et al. | 600/18 |
| 2002/0103413 A1 * | 8/2002 | Bugge et al. | 600/16 |
| 2002/0137981 A1 * | 9/2002 | Williams et al. | 600/18 |
| 2002/0151761 A1 * | 10/2002 | Viole et al. | 600/16 |
| 2002/0169359 A1 * | 11/2002 | McCarthy et al. | 600/16 |
| 2002/0173693 A1 * | 11/2002 | Landesberg | 600/16 |
| 2002/0198436 A1 * | 12/2002 | Hoshino | 600/18 |
| 2003/0023131 A1 * | 1/2003 | Antaki | 600/16 |
| 2003/0032853 A1 * | 2/2003 | Korakianitis et al. | 600/16 |
| 2003/0055309 A1 * | 3/2003 | Kaushansky et al. | 600/18 |
| 2003/0069466 A1 * | 4/2003 | Tsukahara et al. | 600/16 |
| 2003/0069468 A1 * | 4/2003 | Bolling et al. | 600/16 |
| 2003/0083539 A1 * | 5/2003 | Leschinsky | 600/18 |
| 2003/0088147 A1 * | 5/2003 | Bolling et al. | 600/16 |
| 2003/0092961 A1 * | 5/2003 | Korakianitis et al. | 600/16 |
| 2003/0097036 A1 * | 5/2003 | St. Germain et al. | 600/16 |
| 2003/0105383 A1 * | 6/2003 | Barbut et al. | 600/16 |
| 2003/0125601 A1 * | 7/2003 | Schock et al. | 600/18 |
| 2003/0135086 A1 * | 7/2003 | Khaw et al. | 600/16 |
| 2003/0144624 A1 * | 7/2003 | Barbut | 604/8 |
| 2003/0171642 A1 * | 9/2003 | Schock et al. | 600/18 |
| 2003/0176760 A1 * | 9/2003 | El Oakley et al. | 600/16 |
| 2003/0191357 A1 * | 10/2003 | Frazier | 600/16 |
| 2003/0195382 A1 * | 10/2003 | Barbut | 600/16 |
| 2003/0233023 A1 * | 12/2003 | Khaghani et al. | 600/18 |
| 2004/0015043 A1 * | 1/2004 | Frazier | 600/18 |
| 2004/0019251 A1 * | 1/2004 | Viole et al. | 600/16 |
| 2004/0034272 A1 * | 2/2004 | Diaz et al. | 600/18 |
| 2004/0059179 A1 * | 3/2004 | Maguire et al. | 600/16 |
| 2004/0059183 A1 * | 3/2004 | Jansen et al. | 600/17 |
| 2004/0064090 A1 * | 4/2004 | Keren et al. | 604/96.01 |
| 2004/0064091 A1 * | 4/2004 | Keren et al. | 604/96.01 |
| 2004/0073080 A1 * | 4/2004 | Peters et al. | 600/18 |
| 2004/0092789 A1 * | 5/2004 | Tsukahara et al. | 600/16 |
| 2004/0097782 A1 * | 5/2004 | Korakianitis et al. | 600/16 |
| 2004/0097783 A1 * | 5/2004 | Peters et al. | 600/16 |
| 2004/0097784 A1 * | 5/2004 | Peters et al. | 600/18 |
| 2004/0116768 A1 * | 6/2004 | Bolling et al. | 600/16 |
| 2004/0122282 A1 * | 6/2004 | Anzellini | 600/16 |
| 2004/0147802 A1 * | 7/2004 | Woodard et al. | 600/16 |
| 2004/0147803 A1 * | 7/2004 | Hegde et al. | 600/16 |
| 2004/0152945 A1 * | 8/2004 | Kantrowitz et al. | 600/18 |
| 2004/0167376 A1 * | 8/2004 | Peters et al. | 600/18 |
| 2004/0230090 A1 * | 11/2004 | Hegde et al. | 600/18 |
| 2004/0236172 A1 * | 11/2004 | Bolling et al. | 600/16 |
| 2004/0236173 A1 * | 11/2004 | Viole et al. | 600/16 |
| 2004/0267086 A1 * | 12/2004 | Anstadt et al. | 600/17 |
| 2005/0020870 A1 * | 1/2005 | Suzuki et al. | 600/16 |
| 2005/0043579 A1 * | 2/2005 | Dae et al. | 600/18 |
| 2005/0049451 A1 * | 3/2005 | Schock et al. | 600/16 |
| 2005/0070755 A1 * | 3/2005 | Zheng et al. | 600/16 |
| 2005/0075531 A1 * | 4/2005 | Loeb et al. | 600/17 |
| 2005/0085685 A1 * | 4/2005 | Barbut | 600/16 |
| 2005/0124849 A1 * | 6/2005 | Barbut et al. | 600/18 |
| 2007/0265490 A1 * | 11/2007 | Smith et al. | 600/18 |

\* cited by examiner

RIGID BODY AORTIC BLOOD PUMP IMPLANT

CROSS-REFERENCE TO RELATED APPLICATIONS

This application is a continuation of U.S. patent application Ser. No. 12/120,457 filed May 14, 2008; now U.S. Pat. No. 8,721,515 B1; that in turn claims priority of U.S. Provisional Patent Application Ser. No. 60/944,292 filed Jun. 15, 2007; and is also a continuation-in-part of U.S. patent application Ser. No. 10/770,269 filed Feb. 2, 2004, which claims priority of U.S. Provisional Patent Application Ser. No. 60/444,077 filed Jan. 31, 2003 and Ser. No. 60/477,740 filed Jun. 11, 2003, the contents of the aforementioned are incorporated herein by reference.

FIELD OF THE INVENTION

The present invention relates generally to an implantable cardiac blood pump and in particular to an implantable blood pump incorporating a shell adapted to extend pump lifetime.

BACKGROUND OF THE INVENTION

Heart disease is one of the leading causes of death. Currently, medical science cannot reverse the damage done to the cardiac muscle by heart disease. The only known solution is a heart transplant. However, the number of cardiac patients in need of a heart transplant far exceeds the limited supply of donor hearts available.

The scarcity of human hearts available for transplant, as well as the logistics necessary to undertake heart transplant surgery, make a permanently implantable cardiac assist device a viable option for many heart patients. An aortic blood pump can be permanently surgically implanted in the wall of the aorta to augment the pumping action of the heart. The aortic blood pump is sometimes referred to as a mechanical auxiliary ventricle assist device, dynamic aortic patch, or permanent balloon pump.

Typically, the aortic blood pump includes a membrane that moves relative to a pump body as the body internal pressure is cycled in a predetermined synchronous pattern with respect to the diastole and systole of the patient to elevate aortic blood pressure immediately after aortic valve closure. Membrane movement can be accomplished by means of an external supply tube connected to the bladder or an implanted supply reservoir. Electrical leads from electrodes implanted in the myocardium are likewise brought out through the skin by means of the PAD. The "R" wave of the electrocardiograph can be employed to control the fluid pressure source to inflate and deflate the inflatable chamber in a predetermined synchronous relationship with the heart action.

The aortic blood pump acts to assist or augment the function of the left ventricle and is typically restricted to use in patients who have some functioning myocardium. The aortic blood pump does not need to be operated full time, and in fact, can be operated periodically on a scheduled on-time, off-time regimen. Typically, the patient can be at least temporarily independent of the device for periods of a few minutes to hours, since continuous pumping is not obligatory.

U.S. Pat. No. 6,471,633 discloses a dynamic aortic patch with an elongate membrane having a semi-rigid shell body portion and a relatively thin membrane portion defining an inflatable chamber. At least one passage extends through the shell body defining an opening in the inner surface of the shell body. The flexible membrane can be continuously bonded to the shell body adjacent the peripheral side edge to define the enclosed inflatable chamber in communication with the passage. The membrane optionally has a reduced waist portion defining a membrane tension zone adjacent to the opening of the passage into the chamber to prevent occluding the entrance while deflating the chamber. An outer layer can be bonded to the outer side of the wall portion of the aortic blood pump and cut with a freely projecting peripheral edge portion to provide a suture ring for suturing the aortic blood pump in place within an incision in the aorta.

The operational lifetime of an implanted pump is a source of constant concern. The constant movement of blood, movement of the vessel wall and the movement of the deflecting membrane relative to the pump shell, all impact pump operational lifetime. There is a continuing need for extending the number of inflation/deflation cycles a pump can support prior to failure so as to make a permanently implantable cardiac assist device a viable option for more heart patients.

SUMMARY OF THE INVENTION

An implantable stable aortic blood pump is provided that has a shell with an intrinsic rigidity that promotes membrane cycling movement control, and as a result extends operational lifetime of the implanted pump. The rigid body of the pump has a wall extending along a long axis and defining an inflation port portion with an inflation aperture therethrough. The aperture is in fluid communication with an inner surface of the body and on a fluid supply. The body has a cantilevered deformation of less than 8 millimeters in response to a 200 gram weight suspended from a front body edge. A deflecting membrane is secured to the body to deflect in response to fluid pressure flow timed so as to pump blood when the pump is secured to a subject aorta. Achieving the desired degree of rigidity without resort to an external brace or external stiffener provides a more uniform stress distribution across the pump body during pump operation as compared to the externally reinforced semi-rigid pump body.

An implantable aortic blood pump is also provided with a rigid body having a wall extending along a long axis and defining an inflation port portion with an inflation aperture therethrough. The aperture is in fluid communication with an inner surface of the body and a fluid supply. The body has a cantilevered deformation of less than 8 millimeters in response to a 200 gram weight suspended from a front body edge. The body has a bead diameter at a bottom edge at least 10% greater in linear dimension than the adjacent body wall cross section. A deflecting membrane secured to the body deflects in response to fluid pressure flow timed to pump blood when the pump is secured to a subject aorta. Achieving the desired degree of rigidity without resort to an external brace or external stiffener provides a more uniform stress distribution across the pump body during pump operation as compared to the externally reinforced semi-rigid pump body.

DETAILED DESCRIPTION OF THE PREFERRED EMBODIMENTS

An implanted aortic blood pump has utility in increasing blood ejection from a compromised heart. An implantable aortic blood pump provided by the present invention includes a pump body adapted to limit deformation, after implantation during dynamic pressure cycling in temporal concert with subject heart rhythm. By limiting cantilevered body wall deflection, membrane creasing induced failure of the inventive pump is delayed relative to existing ventricular assist devices.

Figure 1:
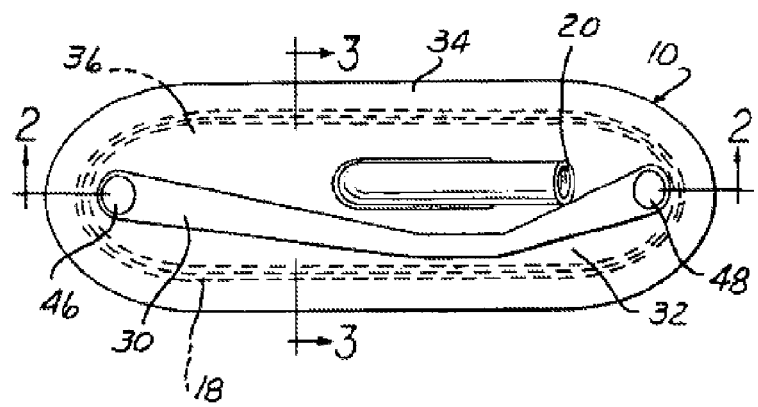
FIG. 1 is a plan view of an aortic blood pump with a stiffening element according to the present invention.

An inventive pump implant improves membrane cycling through forming the pump body from a material that itself provides a desired level of rigidity, so as to have a cantilevered deformation of less than 8 millimeters (mm) linear displacement along the body long axis and preferably less than 3 mm, and more preferably less than 1 mm in response to a 200 gram weight being suspended from the unsupported terminal left edge of the pump body of FIG. 1. Most preferably, the cantilevered deformation is between 0.005 and 0.3 mm. The cantilevered deformation is measured by supporting the bottom surface along edge 18 between the right terminal edge of FIG. 1 and the center of the body 14. An immobile substrate supports the body 14 and terminates parallel to line 3-3 of FIG. 1. The vertical displacement of the left end of FIG. 1 caused by the 200 gram weight is the value used herein to determine linear displacement. The rear half of the body 14 is also expected to deform less than 8 mm according to this protocol and generally match the front half deformation. In a preferred embodiment of an inventive implantable aortic blood pump, the wall is configured to follow the contour of the native human aorta at the point of implantation. A portion of the aorta wall is excised to secure an inventive pump to an aorta. A pump wall that generally follows the arcuate form of the aorta prior to pump implantation is provided to reduce the profile of the body 14 and stresses on the securements between the pump and the aorta.

An aortic blood pump, synonymously described as a permanent blood pump, generally is designated as 10 in FIGS. 1-4. The aortic blood pump 10 according the present invention assists in cardiac function during a cardiac cycle of a patient when positioned with respect to an aorta 12. The aortic blood pump 10 preferably includes an elongate, rigid body 14 having a contoured, concave inner surface 16 terminating at a peripheral side edge 18. At least one passage 20 extends through the body 14 to define an opening 22 in the inner surface 16. An elongate membrane 24 can be continuously bonded to the body 14 adjacent to the peripheral side edge 18. The membrane 24 in deflecting cooperation with the body 14 defines an enclosed inflatable chamber 26 in fluid communication with the passage 20.

A piece of flexible sheet material 32 of a commercially available type and certified for use in implanted devices, or other suitable material, can be bonded to one side of the body 14. The sheet material 32 can be cut generously to provide a peripheral suture ring 34. The ring 34 projects freely from the body 14 to provide a suture ring for implanting the device in an incision in the aorta 12. As previously indicated, the inflatable chamber 26 can be formed with an integral projecting tube portion or passage 20 with a distal end connected to one end of a supply tube (not shown).

Further details regarding the structure and function of the aortic blood pump and associated devices and controls can be obtained from U.S. Pat. No. 6,511,412 issued Jan. 28, 2003; U.S. Pat. No. 6,471,633 issued Oct. 29, 2002; U.S. Pat. No. 6,132,363 issued Oct. 12, 2000; U.S. Pat. No. 5,904,666 issued May 18, 1999; U.S. Pat. No. 5,833,655 issued Nov. 11, 1998; U.S. Pat. No. 5,833,619 issued Nov. 10, 1998; U.S. Pat. No. 5,242,415 issued Sep. 7, 1993; U.S. Pat. No. 4,634,422 issued Jan. 6, 1987; and U.S. Pat. No. 4,630,597 issued Dec. 23, 1986 which are incorporated by reference in their entirety herein.

Figure 2:
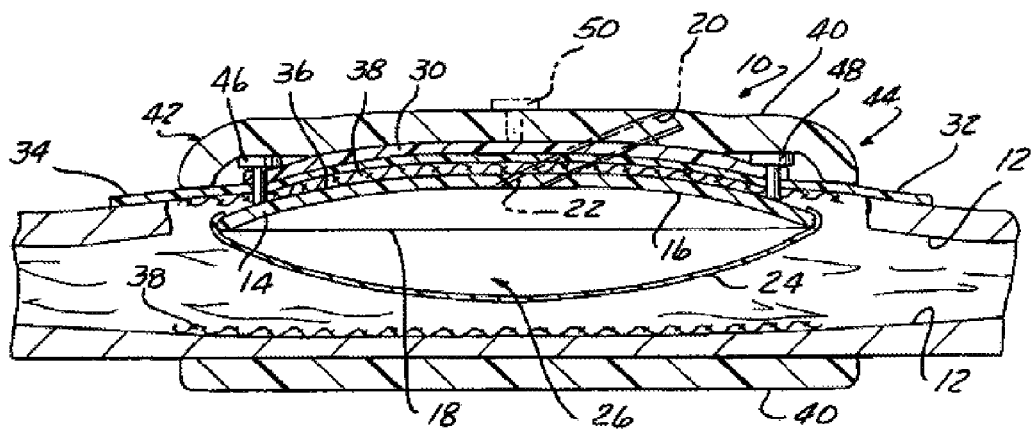
FIG. 2 is a long axis cross-sectional view taken as shown in FIG. 1 illustrating the aortic blood pump in an inflated position and sutured to the wall of an aorta of a patient.
Figure 3:
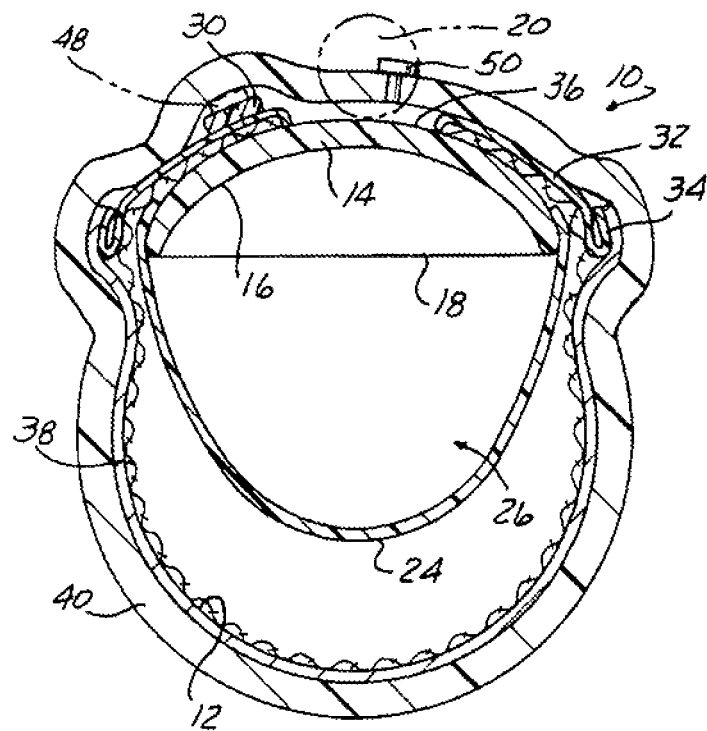
FIG. 3 is a transverse cross-sectional view taken as shown in FIG. 1 illustrating the aortic blood pump in the inflated condition.

Referring now to FIGS. 2-3, the pump 10 is shown in longitudinal and transverse cross-sectional views implanted within the wall of the thoracic aorta 12. The inflatable chamber 26 of the pump 10 is illustrated in an inflated condition in FIGS. 2 and 3. To implant the device, a surgeon makes a longitudinal incision through the wall of the aorta 12, usually downwardly from a location just below the subclavian artery, and the device can be placed within the incision and sewn firmly in position by sutures passing through the projecting suture ring 34 of the sheet material layer 32. The device is optionally implanted with minimally invasive surgical procedures and techniques. The material 32, such as polyethylene terephthalate (DACRON), has a fibrous surface allowing migration into and mechanical interweaving of body tissues to augment the sealing action initially established by the sutures. The polyethylene terephthalate velour or other suitable material layer 32 can be bonded to the outer surface 36 of the body 14 to provide a freely projecting ring 34 used for suturing the device in place after an incision has been made in the aorta 12. The body 14 can be a relatively thick, rigid member 14. The body 14 can be molded from a biocompatible material such as a urethane and incorporates a projecting air inlet tube 20.

As can be seen in the cross-sectional views of FIGS. 2-3, the outer side of the pump 10 as implanted is optionally a relatively thick, rigid body 14 molded from a biocompatible material or any suitable substitute. The body 14 includes the projecting passage 20 formed integrally with the body 14. As can best be seen in the plan view of FIG. 1, the body 14 can have an elongate elliptical shape with an upper or outer surface 36 convex in both longitudinal and transverse directions. The lower or inner surface 16 of body 14 can be concave in both the longitudinal and transverse directions. Preferably, the peripheral side edge 18 can be smoothly rounded throughout an entire extent.

The thin wall membrane 24 can be fixedly secured to the rigid body 14. The membrane 24 can preferably be fixedly secured with respect to the outer surface 36 adjacent the peripheral side edge 18. Preferably, the membrane 24 is free from the peripheral side edge 18 and free from the inner surface 16 of the body 14. For purposes of illustration, membrane 24 and rigid shell 14 are illustrated as if separately formed. Preferably, the inflatable chamber 26 can be formed by known techniques, such as solvation bonding, resulting in the membrane 24 and the rigid body 14 becoming in effect a single unitary structure that changes volume dynamically in a coordinated period relative to myocardial contraction and relaxation.

As is described in greater detail in the prior patents incorporated herein by reference in their entirety, a tube (not shown) can be led from the implanted pump to a percutaneous access device implanted beneath and projecting through a patient's skin. The percutaneous access device allows the tube and, preferably, electrocardiograph leads, to be operatively connected to, or disconnected from an external pump and controller. In operation, the inflatable chamber 26 can be cyclically inflated and deflated with a pressurized gaseous fluid synchronously with a heartbeat of the patient. Preferably, the synchronous cyclical inflation and deflation of the chamber 26 can be based on a set of programmable patient parameters relating to heart function. It is appreciated that acoustic, accelerometric or other direct measure of aortic valve closure is also operative with any of the inventive pump embodiments to provide operational pump synchronicity with a recipient heart.

FIGS. 1-3 show an aortic blood pump including illustrative types of structures adapted to enhance implant stability by resisting deformation in the face of the fluid and mechanical forces to which it is exposed. In an optional embodiment, a first such structure is a stent 38, composed of a wire-mesh material, in the expanded state adjacent to the wall of an aorta 12. It is appreciated that the stent 38 is optionally a drug-eluting stent or a therapeutic peptide treated stent many examples of which are known in the art. FIG. 2 shows this in a cross-sectional view illustrating the body shape as having a convex outer surface 36 with a concave inner surface 16 extending over the full length of the body 14. The cross-sectional view of FIG. 2 illustrates the body 14 with a peripheral side edge 18 tapering at both ends to approximate the geometrical intersection of the body with a substantially cylindrical aorta 12 in a saddle-like configuration. The stent 38 can be attached to the outer surface 36 of the body 14 and extends outwardly to define a substantially open cylindrical area for expansion of the flexible membrane 24.

Figure 4:
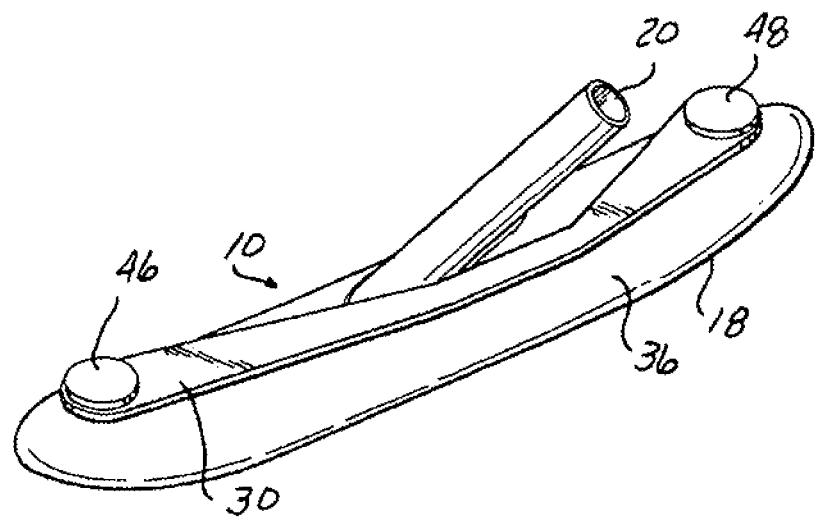
FIG. 4 is a perspective view of the blood pump or aortic blood pump with an attached stiffener according to the present invention.

The rigid body 14 is preferably constructed of a polyurethane or other biocompatible material of sufficient density as to form a rigid structure that is resistant to deflection following insertion into or onto an aorta and exposure to the fluid pressure and flow effects. Biocompatible materials operative herein illustratively include polyurethanes, polycarbonate-urethanes, thermoplastic polyether urethanes, silicone-polyether-urethanes, silicone-polycarbonate-urethanes, fluoropolymers, polyamides, steel, titanium, nitinol, and glass. It is appreciated in that numerous rigid materials are optionally coated with a biocompatible layer such as titanium coated with pyrolytic carbon so that rigidity is maintained while avoiding undesirable bioreactivity. However, in an alternate embodiment at least one elongate arcuate brace 40, which can be molded from a biocompatible material for attachment to the shell or formed integrally with the shell, is used to increase shell rigidity. The brace 40 can be used alone or in combination with a stent 38 or other suitable stiffening apparatus or structure. Opposite ends 42, 44 of the elongate brace 40, as shown in FIG. 2, can be connected to the outer surface 36 of the rigid body 14 to optionally encircle an aorta 12, such that the aorta 12 can be interposed between the brace 40 and the stent 38. By way of example and not limitation, the brace 40 can be connected adjacent one longitudinal end with a living hinge allowing pivoting movement of the brace 40 with respect to the body 14. The opposite end of the brace 40 can be connected to the shell with any suitable type of mechanical connection. By way of example and not limitation, the mechanical connection can be accomplished with an interlocking latch, a heat-stake pin, a screw, or any other suitable fastener known to those skilled in the art. FIGS. 2 and 3 further illustrate a pin 50 to further secure the brace 40 within the inventive pump 10. The illustrated embodiment in FIG. 4 shows the stiffener 30 having an arcuate or angled V-shape secured to the body 14 with mechanical fasteners such as pins 46 and 48. The brace 40 is optionally formed so as to conform to the natural anatomy of the aorta. The stiffener 30 is formed of a material having an intrinsic stiffness greater than that of the material from which the body 14 is formed. It is appreciated that the stiffener 30 is readily encapsulated within the body 14 during the molding process thereof.

Figure 5:
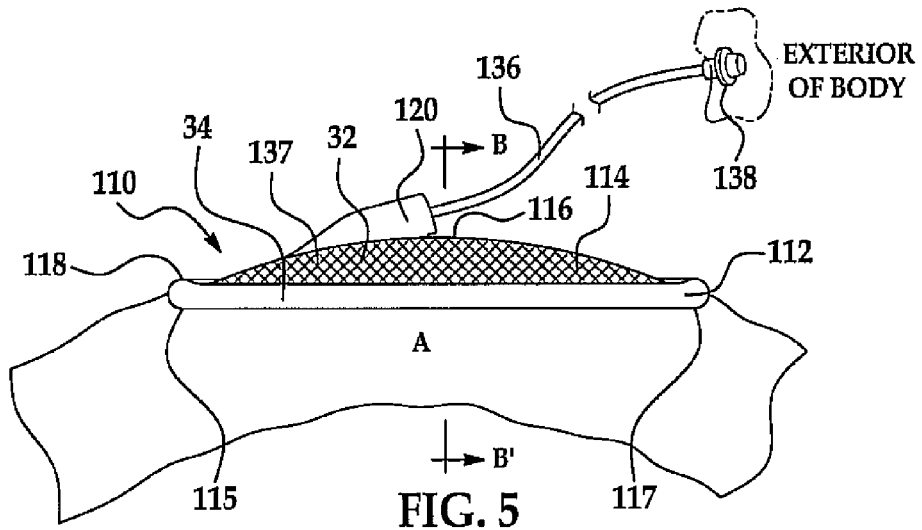
FIG. 5 is a planar view of an alternate inventive unitary body rigid aortic blood pump depicted as positioned relative to a human aorta.
Figure 6:
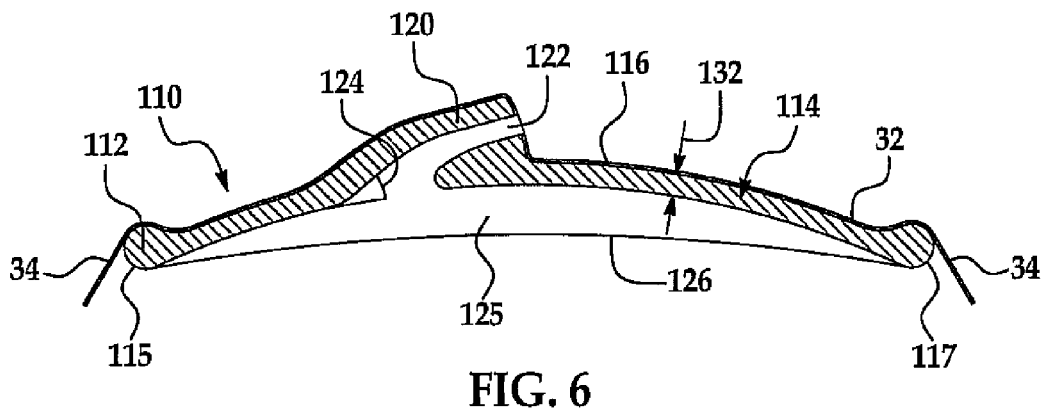
FIG. 6 is a long axis cross-sectional view of the inventive pump depicted in FIG. 5.
Figure 7:
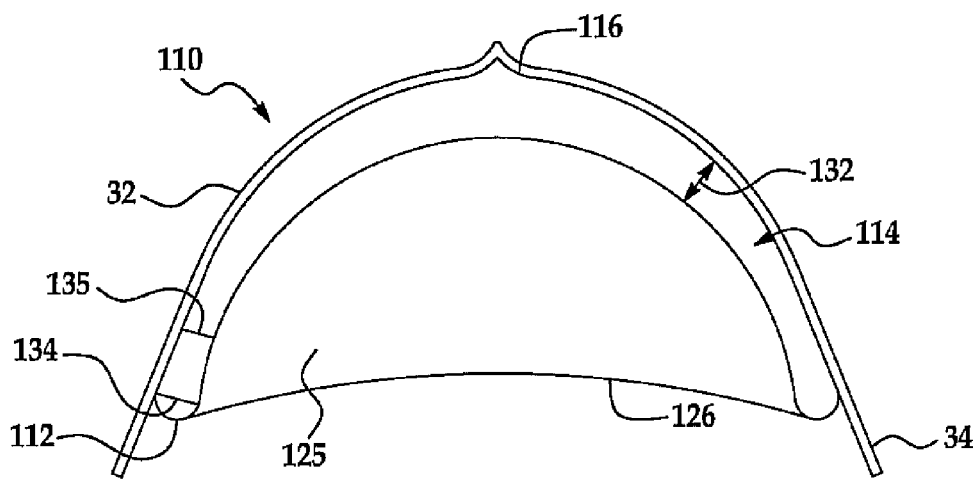
FIG. 7 is a magnified scale central transverse cross-sectional view of the inventive pump of FIG. 6 along plane B-B'.

FIGS. 5-7 show an aortic blood pump including an illustrative structure adapted to maintain implant stability by accommodation of human aortic anatomy. An inventive blood pump as detailed in this embodiment is adapted to conform to the geometry of the human aorta. Referring to the FIGS. 5-7, an embodiment of an inventive blood pump is shown generally at 110. The blood pump 110 is affixed to a human aorta A. In order to accommodate the blood pump 110, a portion of the aorta wall is excised and the blood pump 110 sutured to the aorta A. The body 114 has a generally elliptical bottom surface 112, a top surface 116, and long axis ends 115 and 117. The blood pump 110 typically has a length between ends 115 and 117 of between 3 and 20 centimeters based on the recipient aorta dimensions with neonatal and large adult humans spanning this length range. A preferred length for the pump 110 for an adult human is between 8 and 14 centimeters and corresponding to a dynamic pumping volume of between 30 and 80 cubic centimeters. The dynamic pumping volume is defined as the differential the volume bounded by the membrane with the pump in fully inflated and deflated states. A sheet of material 32 optionally including a suture ring 34 as detailed with respect to FIGS. 1-4 is adhered to convex top surface 116. A line of sutures 118 serves to secure an inventive pump 110 to the aorta A. A gas port housing 120 is integral with the body 114. The gas port housing 120 has an aperture 122 in fluid communication between a fluid supply external to the pump 110 and the interior pump volume 125. The pump volume 125 being defined by the body inner wall surface. Typically, the fluid supply is extracorporeal and connected by way of implanted tubing and a percutaneous access device. Preferably, the gas port housing portion 120 is contoured into the body 114 to inhibit voids in which body fluids may pool. The aperture 122 defines an angle 124 relative to the wall defining the body 114. The angle 124 varies depending on the relative position of a connecting gas tube 136. Typically, the angle 124 is between 10 and 30 degrees. A membrane 126 forms a gas-tight seal with the interior of the body 114. The membrane 126 deflects outward when the gas pressure exceeds the blood pressure within the aorta A within the interior pump volume 125 causing the volume 125 to increase. In contrast to the inventive embodiment of FIGS. 1-4, the pump 110 has a body 114 that itself has an inherent rigidity to achieve a cantilevered deformation of less than 1 mm over either half of the length of the body 114 as measured as according to the protocol provided in the Example. As such an inventive pump 110 is independent of a brace or stiffener per the embodiment depicted in FIGS. 1-4.

Unexpectedly, aortic blood pumps have a body preferably composed of material or are shaped such that the pump possesses a deformation of less than 1 mm along the long axis of the shell. This rigidity is critical to the proper function of the pump without significant deterioration of the pump edge over time. Prior art blood pumps had a degree of flexibility beyond that of the present invention near the pump edge 112, as the conventional wisdom prior to the present invention expected that a semi-rigid body was optimal to allow greater ease in surgical implantation and create a deformable pump that interacts with and continues to translate normal deformation of the aorta itself. However, as the increased rigidity of the instant invention unexpectedly produces longer pump life and fewer patient complications from pump deformation during operation or as a result of hydrodynamic fluid forces. An inventive pump 110 is able to operate during testing in excess of 100 million and preferably 200 million inflation/deflation cycles without complications. 200 million cycles correspond to over 8 years of operation at an 80% duty cycle. Blood pumps lacking the inherent rigidity of pump 110 have a tendency to crease cycling membrane with a resultant loss of performance and a danger of membrane disruption. Thus, the increased rigidity of the instant inventive pump of less than 8 mm and preferably of less than 3 mm, and more preferably less than 1 mm provides the unexpected benefit of increasing operational pump life. Thus, patient recipients experience lower pump failure rates, associated complications, and reduced necessity for pump replacement with the pump 110.

An inventive blood pump body 114 is constructed from any number of biocompatible materials suitable for surgical implantation. Biocompatible materials operative herein illustratively include those detailed with respect to body 14 detailed with respect to the preceding figures.

The choice of material is dictated by the desired pump stiffness, need for operating room formability, skill of the implanting surgeon, and anatomy of the patient. It is appreciated that stiffness of the pump is sufficient to ensure the pump maintains intended geometry once implanted. The pump body 114 according to the present invention is rigid with cantilevered deformation of less than 1 mm linear displacement along the body long axis. Preferably, the cantilevered deformation is less than 3 mm and more preferably less than 1 mm. The cantilevered deformation is measured on a pump body 114 by a protocol of supporting the bottom surface 112 and clamping the longitudinal front half of the pump body (at line B-B' of pump body 110 of FIG. 5) and suspending a 200 gram weight from the terminal edge 115 of the pump body 114. The vertical displacement of the terminal end 115 from which the weight is suspended is the value used herein to determine linear displacement. The rear half of the pump body is likewise formed to have a linear displacement comparable to that of the front half of the pump body.

The blood pump 110 is formed with sufficient stiffness to maintain a desired geometry while experiencing the various forces applied thereto by the aorta and hemodynamic pressure during operation independent of resort to a brace or a stiffener either internal or external to the body per the embodiment depicted in FIGS. 1-4. Inherent rigidity in a unitary body 114 unsupported by a brace or stiffener is optionally derived by varying the thickness 132 of the body 114 as shown in cross-sectional views of FIGS. 6 and 7. A minimal thickness 136 is typically between 2 and 8 mm, and preferably between 3 and 5 mm. It is appreciated that a finite point analysis of the forces exerted on an inventive pump identifies those portions requiring thickness reinforcement in order to obtain desired overall mechanical performance. Generally, the body 114 is thickness reinforced in the region around the top 116 of the pump 110, as well as a thickening along the bottom edge 112 in an amount of between 0 and 50 thickness percent relative to the minimal thickness 136. As such, the bottom surface 112 optionally has a bead diameter 134 that is optionally at least 10% greater in linear dimension than the adjacent cross-sectional wall thickness 136. Preferably, when a bead diameter is increased relative to the minimal thickness 136, the bead diameter 134 is between 20% and 40% greater than the adjacent cross-sectional wall thickness 136. Optionally, the bottom edge 112 is of sufficient thickness to maintain rigidity and integrity of the body 114 shape while being thinner than the adjacent material such that the body tapers from a thickness reinforced portion 132 around the top 116 of the pump that is between 0 and 100 thickness percent thicker relative to the minimal thickness 136 to an equally thick or narrower bottom edge 112. Preferably, the thickness of thickness reinforced portion 132 is between 40 and 80 thickness percent thicker relative to the minimal thickness 136.

An inherently rigid pump body 114 alone or in combination with variation in bead diameter 134 relative to adjacent wall cross section 135 is fashioned by selection of a fiber reinforced organic resin or inorganic material. It is appreciated that adhesion of a membrane 126 to a body 114 formed of a disparate material is facilitated with resort to an adhesive or coating applied to the body 114 that is fusible to the membrane 126.

Example-Pump Body Rigidity Testing and Performance

To document and compare the deflection properties of the blood pump body, a body is mounted in a test apparatus fixture. To prepare a pump body for weighted deflection testing, a piece of string is attached to the rearmost end of each pump back. The string is used to hang weights from the pump body, so care is taken to precisely align the string along the central axis of the pump body. The pump body is secured to a stainless steel plate using adhesive tape. Each pump body tested has a length of 120 millimeters (mm) and is taped to the plate so that the rearmost tip of the pump back extends precisely 60 millimeters over the edge of the plate. A height gauge is used to record deflection of each pump body as a function of weight load. The dial height gauge is accurately zeroed to reflect the no load state of the pump back. If the top surface of the mounting plate is used as a zero reference, the pump body rearmost tip measures zero deflection under no load conditions. Starting with a 20-gram weight, the mass is secured to the string extending from the pump body to measure the tip deflection distance with the height gauge at 23 degrees Celsius. This is repeated with the 50, 100, 200, and 500-gram weights, respectively, and the values recorded.

Using the identical mold that yields a pump substantially as shown in FIGS. 5-7, and designated as Model 009, two pumps were molded from ELASTHANE 80A (Polymer Technology Group, or ELASTHANE 55D (a block copolymer of polyurethane and polyethylene glycol). A third pump body was fabricated using the same pump dimensions fed to a stereolithography tool (SLA) to form a like pump body by photocrosslinking. The photosensitive precursors form a block copolymer of polyurethane and polyethylene glycol of composition comparable to ELASTHANE 75D. The results are provided in Table 1. Pump body ELASTHANE 80A when fitted with a membrane and operated at 80% duty cycle showed excessive membrane creasing after less than 50 million cycles while the ELASTHANE 55D and SLA pump bodies when subjected to the same testing showed membrane stability after in excess of 100 million cycles. Additional duty cycle testing of the inventive ELASTHANE 55D and SLA pump bodies is ongoing.

TABLE 1

Deflection as a function of load for pump bodies.

| mass [g] | force [N] | deflection [mm] |
|---|---|---|
| ELASTHANE 80A Comparative | | |
| 20 | 0.1962 | 1.1 |
| 50 | 0.4905 | 2.4 |
| 100 | 0.981 | 4.3 |
| 200 | 1.962 | 10.4 |
| 500 | 4.905 | 25400000 |
| ELASTHANE 80A | | |
| 20 | 0.1962 | 0.0 |
| 50 | 0.4905 | <0.1 |
| 100 | 0.981 | <1.6 |
| 200 | 1.962 | <3.9 |
| 500 | 4.905 | <6.3 |
| SLA | | |
| 20 | 0.1962 | 0.0 |
| 50 | 0.4905 | 0.0 |
| 100 | 0.981 | 0.0 |
| 200 | 1.962 | 0.0 |
| 500 | 4.905 | 0.0 |

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses are encompassed within the spirit of the invention as defined by the scope of the claims.

The invention claimed is:

1. An implantable aortic blood pump comprising:
a rigid body configured to be attached to a subject's aorta with an inner surface concave in both longitudinal and transverse directions relative to a contact surface with the subject's aorta, said body having a wall extending along a longitudinal axis and following an arcuate form, said body follows a contour of the subject's aorta and defining an inflation port portion with an inflation aperture therethrough, the aperture in fluid communication with an inner surface of said body and a fluid supply, said rigid body being independent of a brace or a stiffener, said rigid body having a cantilevered deformation of less than 7 percent the length of said longitudinal axis in response to a 200 gram weight suspended from a front edge relative to a direction of flow in the subject's aorta of said longitudinal axis, where said fluid supply is extracorporeal and connected by way of an implanted tubing to said rigid body via said inflation aperture; and
a deflecting membrane secured to said rigid body and deflecting in response to fluid communication to pump blood when the pump is secured to the subject's aorta, said deflecting membrane deflecting in excess of 100 million inflation/deflation cycles when secured to the subject's aorta wherein said body defines a dynamic pump volume of from 30 to 80 cubic centimeters.

2. The pump of claim 1 wherein said body has a dimensionally variable thickness along the long axis.

3. The pump of claim 1 wherein said body is formed of a polyurethane or copolymer thereof.

4. The pump of claim 1 wherein the cantilevered deformation is between 0.005 and 3 millimeters.

5. The pump of claim 1 further comprising a sheet material layer adhered to a top surface of said body relative to the contact surface with the subject's aorta.

6. The pump of claim 1 wherein the wall has a minimum thickness of between 2 and 8 millimeters and the wall is formed of a polymer.

7. The pump of claim 6 wherein the wall has a thickness reinforced portion proximal to the inflation port that is thicker than the minimal thickness.

* * * * *